United States Patent
Nguyen et al.

(10) Patent No.: US 7,608,569 B2
(45) Date of Patent: Oct. 27, 2009

(54) PROCESS FOR INHIBITING HAIR FROM BECOMING FRIZZY USING A POLYETHYLENEIMINE/ANIONIC SILICONE MIXTURE

(75) Inventors: Nghi Van Nguyen, Edison, NJ (US); David W. Cannell, Plainfield, NJ (US); Cynthia Chong Espino, Princeton, NJ (US); Sawa Hashimoto, Westfield, NJ (US); Katherine Natalie Barger, Cranford, NJ (US)

(73) Assignee: L'Oréal (FR)

( * ) Notice: Subject to any disclaimer, the term of this patent is extended or adjusted under 35 U.S.C. 154(b) by 479 days.

(21) Appl. No.: 11/280,057

(22) Filed: Nov. 16, 2005

(65) Prior Publication Data

US 2007/0110690 A1     May 17, 2007

(51) Int. Cl.
C11D 3/37      (2006.01)
C11D 9/36      (2006.01)

(52) U.S. Cl. ............... 510/122; 510/119; 510/130; 510/466; 510/477; 510/499; 510/533

(58) Field of Classification Search .......... 510/119, 510/122, 130, 466, 499, 533, 477
See application file for complete search history.

(56) References Cited

U.S. PATENT DOCUMENTS

| 5,070,171 | A | 12/1991 | O'Lenick, Jr. | |
| 5,093,452 | A | 3/1992 | O'Lenick, Jr. | |
| 5,149,765 | A | 9/1992 | O'Lenick, Jr. | |
| 5,248,783 | A | 9/1993 | O'Lenick | |
| 5,739,371 | A | 4/1998 | O'Lenick, Jr. | |
| 6,482,400 | B1 * | 11/2002 | Collin | 424/70.6 |
| 2004/0062737 | A1 * | 4/2004 | Nguyen et al. | 424/70.12 |
| 2004/0063592 | A1 * | 4/2004 | Nguyen et al. | 510/124 |
| 2006/0286057 | A1 * | 12/2006 | Cannell et al. | 424/70.12 |

OTHER PUBLICATIONS

CTFA International Cosmetic Ingredient Dictionary and Handbook, 8th ed. vol. 2, 2000, pp. 1701-1703.

* cited by examiner

*Primary Examiner*—Charles I Boyer
(74) *Attorney, Agent, or Firm*—Lerner, David, Littenberg, Krumholz & Mentlik, LLP

(57) ABSTRACT

A process for inhibiting hair fibers from becoming frizzy, involving contacting the hair fibers with a composition containing: (a) at least one polyamine compound having at least two amino groups; (b) at least one anionic silicone; (c) optionally, at least one surfactant; and (d) optionally, at least one film-forming polymer, and wherein (a) is present in the composition in an amount sufficient to inhibit dyed hair fibers from losing their color, as well as inhibit hair fibers, in general, from appearing frizzy.

14 Claims, No Drawings

PROCESS FOR INHIBITING HAIR FROM BECOMING FRIZZY USING A POLYETHYLENEIMINE/ANIONIC SILICONE MIXTURE

BACKGROUND OF THE INVENTION

The present invention relates to a process for inhibiting hair fibers, including dyed hair fibers, from becoming frizzy when exposed to humidity. The process involves contacting the hair fibers with a composition containing at least one polyamine compound having at least two amino groups and at least one anionic silicone.

Frizz is a phenomenon that causes hair to become unmanageable and appear undisciplined. It is one of the biggest problems encountered when hair is subjected to higher humidity (e.g., relative humidities of 80% and more). This problem is oftentimes exacerbated in people with curly hair, either naturally curly or "permed" curly, leading to what is colloquially termed as a "bad hair day". In such a case, hair loses its natural shape and/or its curl definition. The phenomenon of frizz is also experienced by dyed hair fibers which become frizzy due to the chemical interactions associated with the hair dyeing process.

Thus, it is an object of the present invention to provide a process for inhibiting hair from becoming frizzy.

SUMMARY OF THE INVENTION

In order to achieve these and other advantages, the present invention is drawn to a process for inhibiting hair fibers from becoming frizzy involving contacting the hair fibers with a frizz-inhibiting effective amount of a composition containing:
  (a) at least one polyamine compound having at least two amino groups;
  (b) at least one anionic silicone;
  (c) optionally, at least one surfactant; and
  (d) optionally, at least one film former

DETAILED DESCRIPTION

Other than in the operating examples, or where otherwise indicated, all numbers expressing quantities of ingredients and/or reaction conditions are to be understood as being modified in all instances by the term "about".

"Amino groups" as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

The at least one polyamine compound of the present invention comprises at least two amino groups, preferably at least three amino groups, more preferably at least four amino groups, more preferably at least five amino groups, more preferably at least six amino groups, more preferably at least seven amino groups, more preferably at least eight amino groups, more preferably at least nine amino groups, and more preferably at least ten amino groups.

In one embodiment of the present invention, the at least one polyamine compound may, for example, be chosen from aminated polysaccharides comprising at least two amino groups, such as, for example, hydrolysates (through chemical and/or enzymatic process) of aminated polysaccharides comprising greater than two amino groups. In one embodiment, the at least one polyamine compound may, for example, be chosen from polymers. Suitable polymers for use as the at least one amine compound are polymers comprising at least two amino groups as defined herein. Non-limiting examples of suitable polymers include homopolymers comprising at least two amino groups, copolymers comprising at least two amino groups, and terpolymers comprising at least two amino groups. Thus, the at least one polyamine compound comprising at least two amino groups may be chosen from, for example, polymers comprising at least two amino groups formed from (i) at least one monomer unit comprising at least one amino group as defined herein, and, optionally, (ii) at least one additional monomer unit different from the at least one monomer (i); and polymers comprising at least two amino groups formed from (i) at least one monomer comprising at least two amino groups as defined herein, and, optionally, (ii) at least one additional monomer unit different from the at least one monomer (i). According to the present invention, the at least one additional monomer different from the at least one monomer (i) may or may not comprise at least one amino group as defined herein. A particularly preferred polyamine polymer is chitosan.

In one embodiment of the present invention, the at least one polyamine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines ® 9095, 9030, 9010, 5095, 1595 from BASF.

The polyamine compounds can also be substituted. An example of such a compound is PEG-15 Cocopolyamine from Cognis.

In another embodiment, the at least one polyamine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, 8$^{th}$ edition, vol. 2, (2000). In one embodiment, the at least one polyamine compound comprising at least two amino groups is chosen from wheat protein, soy protein, oat protein, collagen, and keratin protein.

In one embodiment, the at least one polyamine compound comprising at least two amino groups is not chosen from proteins and protein derivatives. In one embodiment, the at least one polyamine compound comprising at least two amino groups is not chosen from compounds comprising lysine, compounds comprising arginine, and compounds comprising histidine. In one embodiment, the at least one polyamine compound comprising at least two amino groups is chosen from compounds comprising lysine, compounds comprising arginine, compounds comprising histidine, and compounds comprising hydroxylysine.

It should be noted that the higher the molecular weight possessed by the polyamine, the greater the degree of anti-frizz realized by the invention.

In the present invention, the at least one polyamine compound is employed in an amount sufficient to inhibit hair fibers from appearing frizzy, especially when exposed to high humidity. Typically, it will be present in an amount of from greater than 0% to 30% by weight, preferably from 5% to 20% by weight, and more preferably from 5% to 10% by weight, based on the weight of the composition as a whole.

In general, non-limiting examples of anionic silicones which may be used in the process of the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

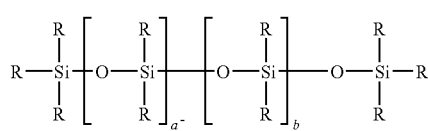
(I)

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

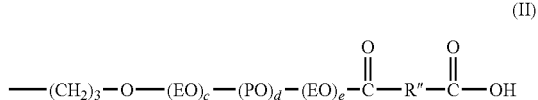
(II)

wherein: c, d, and e, which may be identical or different, are each integers ranging from 0 to 20; EO is an ethylene oxide group; PO is a propylene oxide group; and R″ is chosen from optionally substituted divalent hydrocarbons, such as alkylene groups and alkenylene groups comprising from 2 to 22 carbon atoms, and optionally substituted divalent aromatic groups, such as groups of formula (III):

(III)

and groups of formula (IV):

(IV)

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

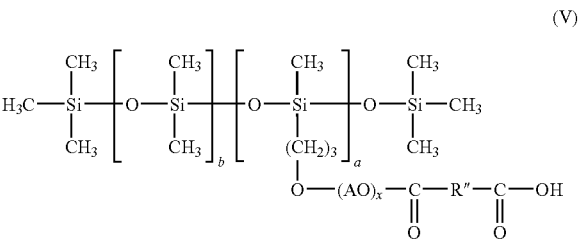
(V)

wherein: a is an integer ranging from 1 to 100; b is an integer ranging from 0 to 500; AO is chosen from groups of formula (VI):

$-(EO)_c-(PO)_d-(EO)_e-$ (VI)

wherein: c, d, and e, which may be identical or different, are each integers ranging from 0 to 20; EO is an ethylene oxide group; and PO is a propylene oxide group; x is an integer ranging from 0 to 60; R" is chosen from optionally substituted divalent hydrocarbons, such as alkylene groups and alkenylene groups comprising from 2 to 22 carbon atoms, and optionally substituted divalent aromatic groups, such as groups of formula (III):

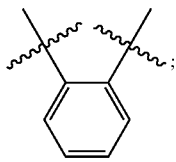

(III)

and groups of formula (IV):

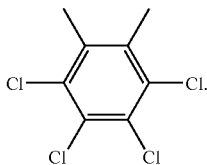

(IV)

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—$CH_2$—$CH_2$—O—) and propylene oxide groups ("PO"=$C_3H_6O$).

The at least one phosphate group may be chosen from terminal phosphate groups and pendant phosphate groups. Further, the at least one phosphate group may be chosen from groups of formula —O—P(O) $(OH)_2$, groups of formula —O—P(O) (OH) (OR), and groups of formula —O—P(O) $(OR)_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (VII):

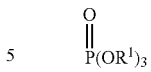

(VII)

wherein $R^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (VIII) and salts thereof:

$CH_3(CH_2)_x$—O-$(EO)_c$—$(PO)_d$-$(EO)_e$—$CH_2CH_2$— (VIII)

wherein: c, and d, which may be identical or different, are each integers ranging from 0 to 20; e is an integer ranging from 0 to 19; and x is an integer ranging from 0 to 21; groups of formula (IX) and salts thereof:

HO-$(EO)_c$—$(PO)_d$-$(EO)_e$—$(CH_2)_x$— (IX)

wherein: c, d, and e, which may be identical or different, are each integers ranging from 0 to 20; and x is an integer ranging from 0 to 21; and groups of formula (X) and salts thereof:

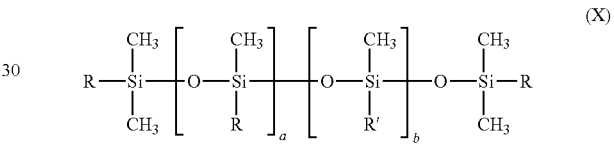

(X)

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (VIII) as defined above and salts thereof, and groups of formula (XI):

-$(EO)_c$—$(PO)_d$-$(EO)_e$—$(CH_2)_3$— (XI)

wherein: the $(CH_2)_3$ end is bonded to the silicon of the compound of formula (X) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (XI) and salts thereof; and with the further proviso that at least one $R^1$ is chosen from groups of formula (X) and salts thereof and at least one other $R^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula XII:

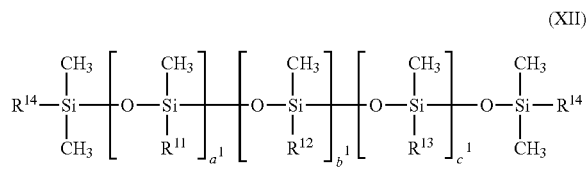

(XII)

wherein $R^{11}$ is selected from lower alkyl having one to eight carbon atoms or phenyl, $R^{12}$ is ——$(CH_2)_3$——O--$(EO)_x$——$(PO)_y$--$(EO)_z$——$SO_3^{31}$-M+ wherein M is a cation and is selected from Na, K, Li, or $NH_4$; x, y and z are integers independently ranging from 0 to 100; $R^{13}$ is ——$(CH_2)_3$——O-$(EO)_x$——$(PO)_y$--$(EO)_z$——H; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula XIII:

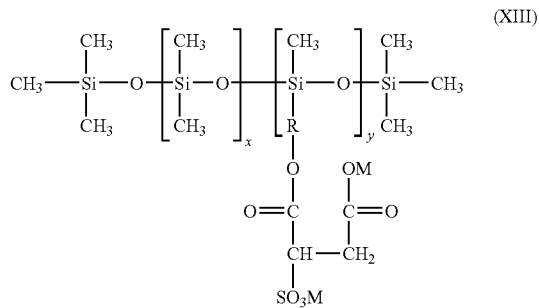

(XIII)

wherein R represents a divalent radical selected from

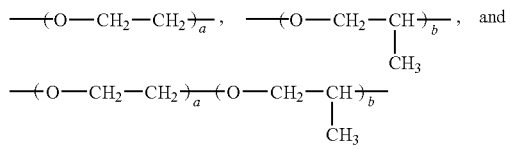

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the tradename Ultrasil PE-100.

The anionic silicone may be employed in an amount ranging from greater than 0 to 50% by weight, preferably from 5 to 30% by weight, and more preferably from 5 to 15% by weight, based on the weight of the composition as a whole.

It may also be desirable to employ various auxiliary ingredients, depending on the type of hair care composition being formulated, i.e., shampoo, conditioner, leave-on/deep treatment, and the like.

For example, when formulating a shampoo, a detersive surfactant will typically be employed in order to impart cleaning capabilities to the compositions. Examples of suitable detersive surfactants include nonionic surfactants, anionic surfactants, amphoteric/zwitterionic surfactants.

Suitable nonionic surfactants are any suitable nonionic surfactants that have an HLB of from about 3 to about 14. The abbreviation "HLB" stands for hydrophilic lipophilic balance. Examples of suitable nonionic surfactants include, but are not limited to, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1-3.

Amphoteric/zwitterionic surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group.

There are a large number of amphoteric surfactants that are suitable for use in this invention. They include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The amphoteric surfactants presently preferred for use in this invention are: cocamidopropyl betaine, coco-betaine, stearyl betaine, cocoamphocarboxyglycinate, cocoamphodipropionate, and stearoamphoglycinate.

The detersive surfactant may be employed in an amount of from greater than 0 to 80% by weight, preferably from 5 to 50% by weight, and more preferably from 10 to 30% by weight, based on the weight of the composition as a whole.

Conditioning agents may also be employed in order to impart added conditioning benefits to the composition. The conditioning agents useful in the present invention are those which are dispersible in water and typically may be chosen from cationic surfactants, silicone compounds, polyalkylene glycols and mixtures thereof, preferably mono long-chain ammonium compounds, hydrophilically substituted cationic surfactants, hydrophilically substituted silicone compounds, polyalkylene glycols, and mixtures thereof.

The type of conditioning agent selected depends on the desired characteristics of the product. Highly water soluble conditioning agents are typically used. A combination of conditioning agents is preferably used to provide benefits provided by the different conditioning agents. Conditioning agents which are less water soluble can be used in combination with highly water soluble conditioning agents.

Cationic surfactants may be used as conditioning agents herein. Suitable cationic surfactants useful herein include, but are not limited to, those generally described as mono long-chain ammonium compounds. Nonlimiting examples of such cationic surfactants include: cetyl trimethyl ammonium chloride available, for example, with tradename CA-2350 from Nikko Chemicals and CTAC 30KC available from KCI, stearyl trimethyl ammonium chloride with tradename Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl amidopropyl trimonium salt, polyoxyethylene alkyl ammonium salt, and mixtures thereof; for example, commercially available under the following tradenames; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

The polyalkylene glycols useful herein as conditioning agents include those which are soluble or dispersible in water. Polyethylene glycols are preferred.

Polyalkylene glycols having a molecular weight of more than about 100 are useful herein. Ethylene oxide polymers are preferred in view of their generally good water solubility, dispersibility, and transparency. Polyethylene-polypropylene glycols and polyoxyethylene-polyoxypropylene copolymer polymers having good dispersibility and transparency may also be useful.

The composition of the present invention may also contain at least one film-forming polymer in order to impart styling and curl retention properties onto the hair. Film-forming polymers useful herein are neutralized, non-neutralized or partially neutralized, polymers and resins, wherein the polymers and resins include but are not limited to those containing carboxyl moieties, such as acrylates and other carboxy polymers.

The following are examples of film forming polymers that can be employed by the present invention. The list is not intended to be limiting:

AMPHOMER LV-71 from National Starch (octylacrylamide/ acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/ methacrylic acid), and ULTRAHOLD STRONG from BASF (acrylic acid/ethyl acrylate/t-butyl acrylamide).

Unneutralized or partially neutralized water-insoluble latexes can also be used as invention film-forming polymers. Included are the following latexes:

AMERHOLD DR-25 from Amerchol (acrylic acid/methacrylic acid/acrylates/methacrylates), LUVIMER 36D from BASF (ethyl acrylate/t-butyl acrylate/ methacrylic acid), and ACUDYNE 258 from Rohm & Haas (acrylic acid/methacrylic acid/acrylates/methacrylates/hydroxy ester acrylates).

The film forming polymer may be employed in an amount sufficient to impart and/or maintain a shape on the hair. Typically, it will be employed in an amount of from greater than 0 to 30% by weight, preferably from 1 to 10% by weight, and more preferably from 1 to 5% by weight, based on total weight of composition.

The composition of the present invention may also comprise additives, for instance those chosen from the non-exhaustive list such as reducing agents, antioxidants, sequestering agents, softeners, antifoams, moisturizers, emollients, basifying agents, plasticizers, sunscreens, direct dyes or oxidation dyes, pigments, mineral fillers, clays, colloidal minerals, nacres, nacreous agents, fragrances, peptizers, preserving agents, fixing or non-fixing polymers, proteins, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The present invention will be better understood from the examples which follow, all of which are intended for illustrative purposes only and are not meant to unduly limit the scope of the invention in any way.

EXAMPLES

Calculation of Frizziness

Virgin hair swatches containing approximately 0.3 grams of hair were cleaned with 0.5 g 15% SLES-2 (pH 6.35). The simple shampoo was massaged into the swatch for 15 seconds and rinsed for 10 seconds with warm water. Swatches were treated with tested solutions then were wound onto pegboards. Swatches were placed in a 50° C. oven for 1 hour and removed to dry and equilibrate to ambient conditions overnight. The next day, the swatches were removed from the pegboards and their photocopies were taken to show their appearance at baseline ($T_0$). Swatches were hung in a humidity chamber set at 90% RH for 2.5 hours. Swatches were removed and final photocopies were taken ($T_{2.5}$). Photocopied images were scanned and digitally analyzed to calculate the percent change in area, % Δ Area, (i.e. degree of frizziness) comparing the square area (in pixels) of baseline and final swatch images. Next, the % Δ Area values were further manipulated to determine the percent less frizz generated by the test solutions compared to water. These calculations were made using the following formulas:

$$\% \, \Delta \, \text{Area (degree of frizz)} = [(T_{2.5} - T_0)/T_0] \times 100$$

$$\% \, \text{Less Frizz Than Water} = 100 - [(\% \, \Delta \text{Area}_{Solution}/\% \, \Delta \text{Area}_{Water}) \times 100].$$

Example 1

Antifrizz of Polyamine/Anionic Silicone as a Leave on Treatment

Virgin hair was treated in quadruplicate with either water or 0.2 g of the following Polyamine/Anionc Silicone water solutions:

A: 3.0% polyvinylamine (Lupamin 9095) and 0.6% dimethicone PEG-8 phosphate, pH 7.2

B: 3.0% polyvinylamine (Lupamin 9030) and 0.6% dimethicone PEG-8 phosphate, pH 7.2

The frizziness was calculated as described above and the results are shown in Table I.

TABLE I

| Antifrizz of Polyamine/Anionic Silicone solutions | |
|---|---|
| Treatment | % Less Frizz Than Water |
| A | 80 |
| B | 80 |

After a single treatment with the various polyvinylamine/anionic silicone solutions, there was a statistically significant improvement in frizz in high humidity conditions compared to those swatches treated with solely water.

Example 2.

Durable Antifrizz of Polyamine/Anionic Silicone Treatment

Hair swatches from Example 1 were shampooed with 15% SLES solution (0.12 g shampoo/swatch) for 15 seconds then rinsed for 10 seconds with warm water. Shampooing was repeated two more times, for a total of three shampoos.

The frizziness was calculated as described above and the results are shown in Table II.

TABLE II

| Percent Less Frizz Than Water of Polyamine/Anionic Silicone solutions after 3 Shampoos | | |
|---|---|---|
| Treatment | After 1 Shampoo | After 3 Shampoos |
| A | 75 | 50 |
| B | 62 | 52 |

After three shampoos with 15% SLES, the anti-frizz effects of the polyvinylamine: anionic silicone solutions proved to be durable in nature, as statistically significant improvements in frizz persisted.

Example 3.

Antifrizz of Polyamine/Anionic Silicone/Film Former in Shampoo

Virgin hair was treated in quadruplicate with 0.5 g of the following Polyamine/Anionc Silicone/Film Former shampoos:

D: Control shampoo containing 2.13% SLES and 12% Disodium Cocoamphodipropionate, pH 7

E: Test shampoo containing 2.13% SLES, 12% Disodium Cocoamphodipropionate, 1% PEI, 0.5% Dimethicone PEG-8 Phosphate, and 0.97% Octylacrylaminde/Acrylates/Butylaminoethylmethacrylate Copolymer, pH 7

The frizziness was calculated as described above and the results showed that, after a single shampoo, those swatches treated with the Test Shampoo E showed significantly less frizz than those treated with the Control Shampoo D by 41%.

Example 4.

Durable Curl Retention of Polyamine/Anionic Silicone/Film Former Solution

Natural virgin hair swatches (1 g swatches, five swatches per treatment) were treated with the following solutions (1 g/swatch):

F: 2% PEI, 0.5% Ultrasil PE-100, 6% Amphomer LV-71 (neutralized to 100% with AMP)

G: 6% Amphomer LV-71 (neutralized to 100% with AMP)

Hair treated with water was also used as a control.

The treated hair swatches were then shampooed with 0.5 g of SLES 10% solution (pH 6.27) for 30 seconds then rinsed for 10 seconds under running water. This was repeated for a total of six shampoos. The hair swatches were rolled onto rollers then placed in the 50° C. chamber for 1 hour, then equilibrated at RT for one hour. The hair was removed from the roller and placed in the humidity chamber for 3 hours at 77% RH. The length of the hair at time 0 and 5 hour was used to calculate the % Curl Retention.

The results are shown in Table III indicating that, after six shampoos, water had worst retention, followed by the film former solution (G), and the Polyamine/Anionic Silicone/Film Former Solution (F) had the best curl retention.

TABLE III

Curl Retention of Hair Treated with Polyamine/Anionic Silicone/Film Former Solution and Shampooed 6 Times

|  | Water | F | G |
|---|---|---|---|
| % Curl Retention | 6.74 | 32.83 | 11.22 |

Example 5.

Durable Curl Retention of Shampoo Containing Polyamine/Anionic Silicone/Film Former Natural virgin hair swatches (5 swatches, 1 g/swatches) were treated with the following shampoo containing 2% PEI, 0.5% Ultrasil PE-100, 1% Amphomer LV-71, 7.6% SLES, 30% Mackam 2CSF 40C: 0.4 g of shampoo was applied to hair, massaged in for 30 seconds then rinsed under running water for 10 seconds. Hair treated with water was also used as a control. The Curl Retention of the hair swatches was determined as described above.

The treated hair swatches were immersed in the water and swished horizontally for 15 seconds and then dunked vertically for 15 seconds. The water immersion was repeated 8 times and the Curl Retention was determined after 4 times dunking and 8 times dunking.

The results are shown in Table IV that hair swatches shampooed with Polyamine/Anionic Silicone/Film Former had much better result than the control and the curl efficiency did not decrease even they were extensively dunked in water.

TABLE IV

Curl Retention of Hair Treated with Shampoo Containing Polyamine/Anionic Silicone/Film Former Before and After Extensive Water Immersion

|  | Water Control | After Shampoo | After 4x Dunking | After 8x Dunking |
|---|---|---|---|---|
| % Curl Retention | 22.84 | 48.73 | 49.93 | 50.66 |

What is claimed is:

1. A process for inhibiting hair fibers from becoming frizzy comprising contacting the hair fibers with a composition containing:
    (a) at least one polyamine compound having at least two amino groups selected from the group consisting of polyethyleneimine;
    (b) at least one anionic silicone;
    (c) optionally, at least one surfactant; and
    (d) at least one film-forming polymer, wherein the film-forming polymer is a different component from components (a) or (b), and wherein (a) is present in the composition in an amount sufficient to inhibit the hair fibers from becoming frizzy.

2. The process of claim 1 further comprising at least one polyamine compound having at least two amino groups selected from the group consisting of polyvinylamine, chitosan, peg-15 copolyloamine, and compounds comprising lysine.

3. The process of claim 1 wherein (a) is present in an amount of from greater than 0 to about 30% by weight, based on the weight of the composition.

4. The process of claim 1 wherein (a) is present in an amount of from about 5% to about 10% by weight, based on the weight of the composition.

5. The process of claim 1 wherein (b) is a silicone phosphate.

6. The process of claim 1 wherein (b) is present in an amount of from greater than 0 to about 50% by weight, based on the weight of the composition.

7. The process of claim 1 wherein (b) is present in an amount of from greater than 0% to about 15% by weight, based on the weight of the composition.

8. The process of claim 1 wherein (c) is an anionic surfactant.

9. The process of claim 1 wherein (c) is present in an amount of from greater than 0% to about 80% by weight, based on the weight of the composition.

10. The process of claim 1 wherein (d) is present in the composition in an amount of from greater than 0% to about 30% by weight, based on the weight of the composition.

11. The process of claim 1 wherein the hair fibers are dyed.

12. The process of claim 1 wherein the composition is a shampoo.

13. The process of claim 1 wherein the composition is a hair conditioner.

14. The process of claim 1 wherein the composition is a hair styling product.

* * * * *

UNITED STATES PATENT AND TRADEMARK OFFICE
CERTIFICATE OF CORRECTION

PATENT NO. : 7,608,569 B2  Page 1 of 1
APPLICATION NO. : 11/280057
DATED : October 27, 2009
INVENTOR(S) : Nguyen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Twelfth Day of October, 2010

David J. Kappos
*Director of the United States Patent and Trademark Office*